US012208150B2

(12) United States Patent
Summers et al.

(10) Patent No.: US 12,208,150 B2
(45) Date of Patent: Jan. 28, 2025

(54) ANTIMICROBIAL SKINCARE COMPOSITION

(71) Applicant: Shielded. Beauty, LLC, Newport Beach, CA (US)

(72) Inventors: Sonia Summers, Newport Beach, CA (US); Maria Corbiscello, New York, NY (US); Kevin O'Brien, Skillman, NJ (US); John Kressaty, La Vergne, TN (US)

(73) Assignee: Shielded, Beauty, LLC, Newport Beach, CA (US)

( * ) Notice: Subject to any disclaimer, the term of this patent is extended or adjusted under 35 U.S.C. 154(b) by 225 days.

(21) Appl. No.: 17/478,773

(22) Filed: Sep. 17, 2021

(65) Prior Publication Data

US 2022/0370309 A1 Nov. 24, 2022

Related U.S. Application Data

(60) Provisional application No. 63/191,315, filed on May 20, 2021.

(51) Int. Cl.

| *A61K 8/19* | (2006.01) |
| *A61K 8/27* | (2006.01) |
| *A61K 8/34* | (2006.01) |
| *A61K 8/365* | (2006.01) |
| *A61K 8/67* | (2006.01) |
| *A61K 8/73* | (2006.01) |
| *A61K 8/9728* | (2017.01) |
| *A61K 8/9789* | (2017.01) |
| *A61Q 17/00* | (2006.01) |
| *A61Q 17/04* | (2006.01) |
| *A61Q 19/00* | (2006.01) |
| *A61Q 19/08* | (2006.01) |
| *A61Q 19/10* | (2006.01) |

(52) U.S. Cl.
CPC ............... *A61K 8/19* (2013.01); *A61K 8/27* (2013.01); *A61K 8/345* (2013.01); *A61K 8/365* (2013.01); *A61K 8/673* (2013.01); *A61K 8/675* (2013.01); *A61K 8/735* (2013.01); *A61K 8/9728* (2017.08); *A61K 8/9789* (2017.08); *A61Q 17/005* (2013.01); *A61Q 17/04* (2013.01); *A61Q 19/007* (2013.01); *A61Q 19/08* (2013.01); *A61Q 19/10* (2013.01)

(58) Field of Classification Search
None
See application file for complete search history.

(56) References Cited

U.S. PATENT DOCUMENTS

| 7,863,417 | B2 | 1/2011 | Ziegler et al. |
| 8,557,249 | B2 | 10/2013 | Brooks et al. |
| 9,375,398 | B2 | 6/2016 | Dreher |
| 10,434,340 | B2 | 10/2019 | Burke-Colvin et al. |
| 10,660,847 | B2 | 5/2020 | Chadwick et al. |
| 10,806,149 | B2 | 10/2020 | Nakamura et al. |
| 2004/0166184 | A1 | 8/2004 | Ghosal |
| 2006/0051385 | A1* | 3/2006 | Scholz ............... A61K 31/155 514/642 |
| 2007/0122492 | A1 | 5/2007 | Behr et al. |
| 2007/0178061 | A1 | 8/2007 | Venturi et al. |
| 2011/0129453 | A1 | 6/2011 | Harripersad |
| 2012/0094914 | A1 | 4/2012 | Maenaka et al. |
| 2014/0178316 | A1* | 6/2014 | Lewis, II ............. A61K 9/0014 424/94.4 |
| 2016/0000088 | A1 | 1/2016 | Nakamura et al. |
| 2018/0318313 | A1 | 11/2018 | Sengupta et al. |
| 2020/0046631 | A1 | 2/2020 | Jin et al. |
| 2020/0214955 | A1 | 7/2020 | Varotto |
| 2020/0268618 | A1* | 8/2020 | Hernandez ........... A61K 8/4953 |

FOREIGN PATENT DOCUMENTS

WO 2013149323 A1 10/2013

OTHER PUBLICATIONS

Touchland, Good-For-You Functional Ingredients, 2021, https://www.touchland.com/pages/ingredients, 3 pages.
Edgar, Jolene et al., The Best Skin-Care Products Infused With Probiotics, Allure, Oct. 10, 2020, https://www.allure.com/gallery/probiotics-skin-care-products, 25 pages.
Brown, Rachel, Phage First: New Brand Ellis Day Skin Science Powers Products With Tiny Bacteria, Brand Report, Apr. 30, 2020, Beauty Independent, https://www.beautyindependent.com/phages-new-brand-ellis-day-skin-science-powers-products-tiny-bacteria-eaters/, 7 pages.
CEW, Indie Spotlight: The Route Combines Medical Grade Skin Care + Luxury Beauty, Beauty News, Jul. 15, 2020, Cosmetic Executive Women, https://www.cew.org/beauty_news/indie-spotlight-the-route-combines-medical-grade-skin-care-luxury-beauty/, 2 pages.
Caldwell, Georgina, Dermalogica Launches Salon Safety Range, Global Cosmetics News, Jul. 21, 2020, Global Cosmetics Media Limited, https://www.globalcosmeticsnews.com/dermalogica-launches-salon-safety-range/, 2 pages.
Brown, Rachel, Skincare for the New Normal: Fortifying + Fighting Bacteria While Providing Beauty Benefits, Brand Report, Feb. 2, 2021, Beauty Independent, https://www.beautyindependent.com/skincare-new-normal-fortify-fighting-bacteria-providing-beauty-benefits/, 6 Pages.

(Continued)

*Primary Examiner* — Nannette Holloman
(74) *Attorney, Agent, or Firm* — MASCHOFF BRENNAN; Elaine K. Lee; Rory J. Radding

(57) ABSTRACT

Embodiments of the present disclosure may include a skincare composition comprising an antimicrobial component, an antiaging component and a moisturizing component comprising at least one alpha-hydroxy acid. A treatment method for improving skin may include administering to an area in need thereof a composition comprising an effective amount of an antimicrobial component, an antiaging component and a moisturizing component comprising at least one alpha-hydroxy acid.

35 Claims, No Drawings

(56) References Cited

OTHER PUBLICATIONS

Skinfix Inc, Barrier+ Triple Lipid-Peptide Cream, Skinfix, 2021, https://skinfix.com/collections/moisturizers/products/lipid-peptide-cream?variant=19409094115397, 6 pages.

"Vitamin C", Wikipedia, last edited on May 14, 2021, https://en.wikipedia.org/w/index.php?title=Vitamin_C&oldid=1023062623, 26 pages.

International Search Report and Written Opinion, International Application No. PCT/US22/29050, mailed Oct. 6, 2022, 17 pages.

* cited by examiner

ANTIMICROBIAL SKINCARE COMPOSITION

CROSS REFERENCE TO RELATED APPLICATIONS

This application claims priority to U.S. Provisional Application No. 63/191,315 filed May 20, 2021. The entire contents of that application are hereby incorporated herein by reference.

BACKGROUND

The present invention relates generally to a cosmetic or dermatological antimicrobial composition and treatment.

Environmental assault on the body and skin is of increasing concern in a world of rapid climate changes. Yet, environmental assault is not limited to just the sun, changing temperatures, and pollution. As the COVID-19 pandemic spread throughout the world in 2019 and 2020 and beyond, the invisible threat of airborne pathogens became suddenly and irrevocably very real. Such airborne pathogens may be characterized as bacteria or viruses, and are typically dispersed into the air from one victim to the next, without physical contact and sometimes, through the ordinary sloughing of the skin. Skin is the largest organ of the human body, and thus healthy skin is extremely important for the good health of every person. If a person's skin is compromised in any way, harmful airborne pathogens can be absorbed into the epidermis and cause inflammation, dehydration, loss of elasticity and firmness.

These threats are increasingly being recognized by many consumers as a result of their adverse experiences during the worldwide COVID-19 coronavirus pandemic. Health and safety considerations are now often of primary importance to consumers during the pandemic, where in the past aesthetic benefits of skin care treatments were considered key purchase drivers. Skin care products that are focused on killing germs, supporting immunity and overall health promotion are more relevant than ever, although such products that also claim naturalness, sustainability, quality and brand provide further unique and differentiated solutions to caring for a person's skin. Families of all sizes, with a diverse mix of generations and cultures, are focusing on day-to-day health and safety needs, and are driven by safety, quality, and the latest in technology as values for skin health.

Current skin care treatment products and methods, however, often lack safety and hygiene-forward solutions that help destroy harmful pathogens and foster a healthy skin microbiome.

The human microbiome comprises trillions of microorganisms (also called microbiota or microbes) of thousands of different species inside the human body. These include not only bacteria but fungi, parasites, and viruses. In a healthy person, these "bugs" coexist peacefully, with the largest numbers found in the small and large intestines but also throughout the body. The microbiome is even labeled a supporting organ because it plays so many key roles in promoting the smooth daily operations of the human body.

Each person has an entirely unique network of microbiota that is originally determined by one's DNA. A person is first exposed to microorganisms as an infant, during delivery in the birth canal and through the mother's breast milk. Exactly which microorganisms the infant is exposed to depends solely on the species of microorganisms found in the mother. Later on, environmental exposures and diet can change one's microbiome to be either beneficial to health or place one at greater risk for disease. See Ursell, L. K., et al. Defining the Human Microbiome. Nutr Rev. 2012 August; 70(Suppl 1): S38-S44.

The microbiome consists of microbes that are both helpful and potentially harmful. Most are symbiotic (where both the human body and microbiota benefit) and some, in smaller numbers, are pathogenic (promoting disease). In a healthy body, pathogenic and symbiotic microbiota coexist without problems. But if there is a disturbance in that balance—brought on by infectious illnesses, certain diets, or the prolonged use of antibiotics or other bacteria-destroying medications—dysbiosis occurs, stopping these normal interactions. As a result, the body may become more susceptible to disease.

Human skin is home to millions of bacteria, fungi and viruses that compose the skin microbiota. Similar to those in the human gut, skin microorganisms have essential roles in the protection against invading pathogens, the education of the human immune system and the breakdown of natural products. As the largest organ of the human body, skin is colonized by beneficial microorganisms and serves as a physical barrier to prevent the invasion of pathogens. In circumstances where the barrier is broken or when the balance between commensals and pathogens is disturbed, skin disease or even systemic disease can result. Human skin sites can be categorized by their physiological characteristics, that is, whether they are sebaceous (oily), moist or dry. Functioning as the exterior interface of the human body with the environment, skin acts as a physical barrier to prevent the invasion of foreign pathogens while providing a home to the commensal microbiota. See Byrd, A., Belkaid, Y. & Segre, J. The human skin microbiome. Nat Rev Microbiol 16, 143-155 (2018). https://doi.org/10.1038/nrmicro.2017.157.

Environmental assault on the skin is thus an increasing concern in a world of rapid environmental and climate changes. As mentioned above, skin is the body's largest organ and the first line of defense against damage from external environmental aggressors such as the sun, pollution, and airborne pathogens, among others. People on average touch their face at least 23 times per hour, which is a major way that viruses and bacteria spread. Furthermore, viral and bacterial pathogens are typically dispersed into the air through ordinary sloughing of the skin and land on facial skin of others. While hands can be washed and sanitized, over-washing or sanitizing frequently damages a person's skin, not just skin on the hands and body, but particularly the more delicate and sensitive facial skin areas. Thus, a skin care regimen is needed that includes skin care compositions focused on not just purification and nourishment of a person's skin, but also shielding the person from environmental aggressors of pollution, adverse temperature and climate conditions, and harmful pathogens, while also protecting skin's natural healthy microbiome. Frequent hand washing and use of hand sanitizer advised by epidemiologists, public health and other medical experts during the coronavirus pandemic does little to combat viral pathogens which land on the face—accessing and ultimately infecting the body via touching the eyes, nose, and mouth. Such airborne pathogens are less easily eradicated without damaging the skin through over-washing or alcohol-heavy formulations that can irritate delicate skin, particularly near the eyes, nose and mouth on the face.

As noted above, when skin is compromised, these pathogens can be absorbed into the epidermis and cause inflammation, dehydration, loss of elasticity and firmness, among other skin and health problems. Current skin compositions and treatments available on the marketplace fail to adequately address all the above problems. The present invention provides a composition and treatment for skin purification, nourishment, and protection from environmental aggressors.

SUMMARY

Some embodiments of the present invention provide a skincare composition comprising an antimicrobial component, an antiaging component and a moisturizing component comprising at least one alpha-hydroxy acid.

Some embodiments of the present invention provide a treatment method for improving skin by administering to an area in need thereof a composition comprising an effective amount of an antimicrobial component, an antiaging component and a moisturizing component comprising at least one alpha-hydroxy acid.

Some embodiments of the present invention provide a treatment method for improving skin by administering to an area in need thereof multiple compositions, comprising cleaning the area with a cleanser composition comprising at least one of ecodermine, lactic acid, vitamin B3, and vitamin B5. The treatment comprises moisturizing the area with a lotion composition comprising at least one of EcoG, EnergiNius®, Hydrolyzed Sodium Hyaluronate, copper ferment, lactic acid, Vitamin B3 (Niacinamide), CityStem™ (Glycerin and *Marrubium Vulgare* Extract) and Sodium Hyaluronate. The treatment comprises misting the skin with a misting composition comprising at least one of EcoG™, Hydrolyzed Sodium Hyaluronate, copper ferment, lactic acid, Marigold (*Calendula officinalis*) Extract, allantoin, Vitamin B3 (Niacinamide), Vitamin B5 (Panthenol), sodium PCA. The treatment comprises cleaning the area with the cleanser and applying a night serum composition to the area, the night serum comprising at least one of propandiol, glycerin, betaine, xanthan gum, distilled water, sodium PCA, Allantoin, ESP Vegabead ProS (*Hansenula, Kloeckera, Lactobacillus, Lactococcus, Leuconostoc, Pediococcus, Saccharomyces*, Fig, Lemon Ferment, Sorbitan Oleate, Cellulose Gum, Chitosan Citric Acid, Water, Glycerin, and Isoeicosane), Synchrolife™ (glycerin, pentylene glycol, rosemary leaf extract, palmitoyl tetrapeptide-7, and chrysin), Makigreen LCS+(caprylyl/capryl glucoside, polyglyceryl-10 isostearate, and sodium dilauramidoglutamide lysine), Lavender and Lemongrass essential oil blend, and Spectrastat G2N MB (caprylhydroxamic acid, glyceryl caprylate, and glycerin). The treatment method may be administered on a daily basis in some embodiments of the invention.

Some embodiments of the present invention provide a composition comprising at least one alpha hydroxy acid selected from the group consisting of lactic acid, citric acid, tartaric acid, citric acid, malic acid, glycolic acid, gluconic acid, salicylic acid and mixtures thereof, at least one blue light mitigator selected from the group consisting of *Withania somnifera* root extract, Marigold (*Calendula officinalis*) Extract, *Scenedesmus rubescens* extract and niacinamide PC, at least one hyaluronic acid selected from the group consisting of hydrolyzed sodium hyaluronate, at least one antioxidant selected from the group consisting of *saccharomyces* copper ferment, and at least one silver zeolite.

DETAILED DESCRIPTION

Embodiments of the invention utilize a novel skin care treatment regimen to protect and strengthen a user's skin microbiome. The novel skin care treatment regimen proposed in embodiments of the present invention comprises the application of several products formulated to each have a distinct purpose in a person's individual skincare regimen. As noted above in the Background section, the human skin (microbiome) is comprised of trillions of bacteria and other microbes. Any disruption to the skin's ecosystem (bacteria that lives on a person's skin) can result in skin disorders or even infection—with this in mind, protection and strengthening of a person's skin is of primary importance.

In one embodiment of the invention, the collection of compositions and products proposed herein works well as a system. In some embodiments of the invention, the individual compositions or products described herein may provide beneficial effects when each product is used alone or in combination with one or more of the other products.

Exemplary Skin Care Regimen

Some compositions disclosed herein can be applied to the skin and remain on the skin for a period of time (e.g., at least 1, 2, 3, 4, 5, or 10 minutes or more). After which, the composition, if needed, can be rinsed from the skin or blotted from the skin with a dry or damp cloth or paper towel. Some compositions disclosed herein can be applied to the skin and immediately rinsed from the skin. Some compositions disclosed herein can be applied to the skin and absorbed at least in part by the skin. These and other non-limiting aspects of the present invention are described below. In one or more embodiments of the invention, a skin care regimen is proposed to protect and strengthen a human's skin:

Step 1—Start with cleansing at the beginning of the day (when waking up) and night (right before bed) as the first step to a user's skin care routine. A prebiotic cleanser having a creamy texture is used in embodiments of the present invention and comprises a cleanser to strengthen the skin at the beginning of the day with a protective skin care regime. The cleanser may comprise a scent—a citrus blend of essential oils to refresh and soothe the user's senses. The cleanser in the embodiments of the present invention incorporates an effective dose of prebiotics (e.g., food for the beneficial bacteria and microbes) to provide the facial skin with nourishment needed for a balanced complexion. In some embodiments of the invention, lactic acid is added to gently exfoliate and reduce pore size, while vitamins B3 (Niacinamide) and B5 (Panthenol) are added for nourishment, and Hydrolyzed Hyaluronate for added hydration. Allantoin is included as an ingredient for many users that have sensitive skin—this ingredient helps to ward off irritation. In one embodiment of the present invention, the cleanser may comprise an everyday product that a user may use for both day and night.

Step 2—After cleansing, the next step in the skin care regimen for embodiments of the present invention comprise skin moisturizing and protection. A moisturizer is used in embodiments of the present invention to combat environmental assault users live through every day—pollution, blue light (digital) and airborne pathogens. The moisturizer used in some embodiments of the present invention comprises a rejuvenating treatment that also soothes the senses. A light yet ultra-moisturizing lotion is formulated in embodiments of the present invention, armed with a novel Guardian Complex™ a blend of ingredients that protect and strengthen a user's skin, including a citrus essential oil, which has a soothing and energizing scent. In some embodiments of the invention, the Guardian Complex formula includes peptides to relieve skin wrinkles, antioxidants to address damaging free radicals, and Vitamins B3 and B5 to brighten, smooth and nourish the user's skin. Hydrators like Hydrolyzed Sodium Hyaluronate and Sodium PCA are also included.

Step 3—In some embodiments of the present invention, the user's skin is refreshed throughout the day in a Purifying Mist, comprising a fine mist spray formula that may be applied under or over a user's make-up, or used without make-up. The purifying mist formulated for embodiments of the present invention protects and strengthens a user's microbiome by adding ingredients with natural antimicrobials, blue light and free radical chasers, hydrators, peptides, and potent hydrators. The purifying mist may be used to refresh throughout the day to keep the user's skin protected, nourished and strengthened.

Step 4—In some embodiments of the present invention, a hand and body shield and purifying lotion comprises a formula that helps to guard and support a user's skin that is exposed to the harsh environmental elements throughout the day. In some embodiments of the present invention, the hand and body shield and purifying lotion includes the innovative Guardian Complex™ described herein, in a specially formulated hand and body lotion that is richer and made for a user's body. The hand and body shield and purifying lotion includes natural anti-microbials, antioxidants, peptides, hydrolyzed hyaluronate, plus lactic acid, vitamins B3 & B5 and Allantoin. The Hand & Body Shield and Purifying Lotion of embodiments of the present invention shields a user's skin from environmental invaders but also seals in nourishing and rejuvenating active ingredients.

Step 5—After a full day of battling environmental factors, a user's skin needs to rest and allow the skin to regenerate. In some embodiments of the present invention, a user's skin is nourished with "good" and beneficial bacteria in order to bring balance to a user's skin during sleep. A Night-Life "Live Probiotic"+HA Serum of some embodiments of the present invention comprises a hydrating treatment that includes "encapsulated live probiotics", where there is no need to refrigerate the serum—it is a stable version in an aqueous and hydrating solution containing Hyaluronic Acid. Another novel aspect of this serum is that it contains Synchrolife™ (e.g., as manufactured by Sederma, comprising Glycerin, Pentylene Glycol, *Rosmarinus Officinalis* (Rosemary) Leaf Extract, Palmitoyl Tetrapeptide-7, Chrysin). These ingredients work together to relax a user's skin in synchronization with a user's circadian rhythms.

Exemplary Skin Care Compositions and Formulations

Some embodiments of the present invention provide a skincare composition comprising an antimicrobial component, an antiaging component and a moisturizing component comprising at least one alpha-hydroxy acid. In some embodiments, the antimicrobial component comprises a silver citrate and zeolite blend. In some embodiments, the blend is at 5% relative to total weight of the composition. In some embodiments, the antiaging component comprises at least one hydrolyzed sodium hyaluronate. In some embodiments, the skincare composition further comprises at least one of an antioxidant component, a vitamin component, and a copper ferment. In some embodiments, the alpha-hydroxy acid comprises at least one of lactic acid, tartaric acid, citric acid, malic acid, glycolic acid, gluconic acid, and salicylic acid.

In some embodiments, the skincare composition further comprises a screen-emitted artificial visible light protecting component comprising at least one of EnergiNius® (e.g., as manufactured by Gattefosse, comprising Fructose, Glycerin, Water, and *Withania somnifera* root extract), *Withania somnifera* root extract, Marigold (*Calendula officinalis*) Extract, PEPHA®-AGE (e.g., as manufactured by DSM Nutritional Products LLC, comprising *Scenedesmus rubescens* extract), and niacinamide (vitamin B3).

In one embodiment of the present invention, EnergiNius® is used to protect skin cells from screen-emitted artificial visible light. After use, the skin may appear visibly revived, and the signs of fatigue may disappear in favor of a healthy glow. In one embodiment of the present invention, EnergiNius® is used in an effective amount, for example at 1%, in facial care formulations.

In some embodiments of the present invention, PEPHA®-AGE reduces blue light (e.g., screen-emitted artificial visible light) induced skin hyperpigmentation and redness, reduces oxidative stress and carbonylated proteins, as well as restores and boost collagen synthesis (especially Collagen III). *Scenedesmus rubescens* is a microalga, a unicellular organism living in freshwater lakes. This microalgal cell has developed self-defense capabilities, with a very strong cell wall protecting against the harsh environment, and with red dots of carotenoids to fight against blue light. *Scenedesmus rubescens* has a chemical composition including amino acids, vitamins (B3), algal saccharides and minerals (Zn). In some embodiments of the present invention, skincare compositions comprising *Scenedesmus rubescens* extract minimize the appearance of aging after exposure to blue light and UV, deliver even skin tone and overall improved skin appearance, and reduces skin damage caused by blue light and UV.

In some embodiments, the antimicrobial component comprises at least one or more of: Hypochlorous Acid, Oregano, Benzochloride, Aloe Vera, Peppermint Extract, Rosemary Extract, Ginger, Manuka Honey, Tea Tree Oil, *Coleus forskohlii* root oil, *Kaempferia galanga* root extract, *Olea europaea* leaf extract, *Curcuma longa*, Silver Citrate, Zeolite, *Melia* azadirachta, *Camellia sinensis* leaf extract, Silver, and Colloidal Silver.

In some embodiments, silver and colloidal silver are an organic and natural antimicrobial ingredient that can be used in skincare compositions described in the present invention, having antibacterial and antifungal properties, with colloidal silver also having a soothing and purifying effect. Examples of other metals that may be used as antimicrobial components of the skincare composition of embodiments of the present invention include copper and copper tripeptides, having similar healing properties as silver, protecting the skin from potential free radical damage, but on a smaller and more cost-effective scale; and zinc oxide, another metal ion known to protect against UVA and UVB rays.

EcoG+ Liquid 100 (comprising Silver Citrate and Zeolite) as used in embodiments of the present invention provides additional benefits over silver and colloidal silver. During manufacturing, any potentially harmful ions are destroyed, leaving behind only the silver ions and the EcoG+ polymer—which acts as a carrier and preservative for the silver in the skincare composition of embodiments of the present invention. Silver ions used in the EcoG+ Liquid 100 (compared to those in colloidal silver and nano-silver) are less likely to cause any type of negative reaction, making Silver EcoG+ suitable for all skin types, and will promote and support skin healing and overall skin health in those with sensitive skins or compromised skin barriers. EcoG+ Liquid 100 is a water-based silver ion protection system that also comprises a strong bactericide providing additional antimicrobial activity alone or in combination with sodium benzoate and other common preservatives. EcoG+ Liquid 100 offers wide pH compatibility and is an all-natural antimicrobial skin purifier suitable for even the most sensitive of skins. See, e.g., Degen, G., 2016. Opinion of the Scientific Committee on Consumer Safety (SCCS)—Final version of the opinion on Eco G+ in cosmetic products. Regulatory Toxicology and Pharmacology, [online] 82, p. 157. Available at: https://ec.europa.eu/healthiscientific_committees/consumer_safety/docs/sccs_o_19 8.pdf.

In some embodiments, the antiaging component comprises at least one or more of: *Dracaena cambodiana* Leaf Extract (Dragons Blood), Copper *Saccharomyces*, Acetyl hexapeptide 3, Acetyl hexapeptide 8, Acetyl hexapeptide 20, Palmitoyl pentapeptide, Palmitoyl oligopeptide, Tripeptide 1, Acetyl tetrapeptide-9, Vitamin C, Vitamin A, Vitamin E, Resveratrol, Coenzymeq10, Niacinamide, Polyphenols, Flavonoids, Glutathione, Peony Extract, Malachite Extract, Hydrolyzed Sodium Hyaluronate, Hydrolyzed Hyaluronate.

In some embodiments, the moisturizing component comprises at least one or more of: Lactic Acid, Tartaric Acid, Citric Acid, Malic Acid, Glycolic Acid, Gluconic Acid, and Salicylic Acid.

Some embodiments of the present invention provide a treatment method for improving skin by administering to an area in need thereof a composition comprising an effective amount of an antimicrobial component, an antiaging component and a moisturizing component comprising at least one alpha-hydroxy acid.

Some embodiments of the present invention provide a treatment method for improving skin by administering to an area in need thereof multiple compositions. The treatment method comprises cleaning the area with a cleanser composition comprising at least one of Ecodermine™, lactic acid, vitamin B3, and vitamin B5, moisturizing the area with a lotion composition comprising at least one of EcoG+ Liquid 100, silver, colloidal silver, *Withania somnifera* root extract, Hydrolyzed Sodium Hyaluronate, copper ferment, lactic acid, allantoin, vitamin B3 (Niacinamide), vitamin B5 (Panthenol), Sodium Hyaluronate; misting the skin with a misting composition comprising at least one of EcoG+ Liquid 100 (Silver Citrate (and) Zeolite), Hydrolyzed Sodium Hyaluronate, copper ferment, lactic acid, Marigold (*Calendula officinalis*) Extract, allantoin, Vitamin B3 (Niacinamide), Vitamin B5 (Panthenol), and sodium PCA; cleaning the area with the cleanser; and applying a night serum composition to the area, the night serum comprising at least one of propanediol, glycerin, betaine, xanthan gum, distilled water, sodium PCA, Allantoin, ESP Vegabead ProS (e.g., as manufactured by Earth Supply Products; comprising *Hansenula, Kloeckera, Lactobacillus, Lactococcus, Leuconostoc, Pediococcus, Saccharomyces*, Fig, Lemon Ferment, Sorbitan Oleate, Cellulose Gum, Chitosan, Citric Acid, Water, Glycerin, and Isoeicosane), Synchrolife™ (e.g., as manufactured by Corda (Sederma) comprising glycerin, pentylene glycol, rosemary leaf extract, palmitoyl tetrapeptide-7, and chrysin), Makigreen LCS+(e.g., as manufactured by KOBO; comprising caprylyl/capryl glucoside, polyglyceryl-10 isostearate, and sodium dilauramidoglutamate lysine), Lavender and Lemongrass essential oil blend (e.g., as manufactured by Premier Specialties), and Spectrostat G2N MB (e.g., as manufactured by Inolex; comprising caprylhydroxamic acid, glyceryl caprylate, and glycerin).

The vitamin $B_3$ added in some embodiments of the present invention provide significant benefits in regulating skin condition, especially in therapeutically regulating signs of skin aging, more especially wrinkles, lines, and pores. See U.S. Pat. No. 8,557,249.

As used in some embodiments of the present invention, Ecodermine™ (e.g., as manufactured by Sederma) is a composition of two complementary active ingredients, Lactitol and Xylitol, dissolved in glycerin. Cosmetically, it is used in soaps, shower gels and shampoos. The composition of Lactitol and Xylitol fights skin problems due to microbial disequilibrium by helping to preserve the skin's natural defense mechanisms. It preserves and restores selectively the cutaneous microflora.

Some embodiments of the present invention provide a composition (that may be known also by a tradename of Guardian Complex™) comprising at least one alpha hydroxy acid selected from the group consisting of lactic acid, citric acid, tartaric acid, citric acid, malic acid, glycolic acid, gluconic acid, salicylic acid and mixtures thereof, and may be used as exfoliating agents in one embodiment of the present invention. Other exfoliating agents known to those skilled in the art are also contemplated as being useful within the context of the present invention.

The composition may further comprise at least one blue light mitigator selected from the group consisting of *Withania somnifera* root (Indian *ginseng* root) extract, Marigold (*Calendula officinalis*) Extract, *Scenedesmus rubescens* extract and niacinamide PC. The composition may further comprise at least one hyaluronic acid selected from the group consisting of hydrolyzed sodium hyaluronate, hydrolyzed hyaluronic acid, sodium acetylated hyaluronate, and sodium hyaluronate. The composition may further comprise at least one antioxidant selected from the group consisting of *saccharomyces* copper ferment. The composition may further comprise at least one silver zeolite.

In some embodiments, the composition further comprises ingredients selected from a group consisting of Ecodermine™, Marigold (*Calendula officinalis*) Extract, allantoin, niacinamide, panthenol, hyaluronic acid, prebiotics, probiotics, CityStem™, sodium PCA, sodium hyaluronate, hydrolyzed hyaluronate, Synchrolife™, and combinations thereof.

In some embodiments, the composition or some of its ingredients may be included in various cosmetic or dermatological product types including moisturizers, serums, mists, lotions, cleansers, balms, masks and the like. According to some embodiments, the composition or ingredients thereof, focuses on defending and strengthening the skin's microbiome from environmental assault.

As used in some embodiments of the present invention, *Saccharomyces* Copper Ferment is a yeast extract with copper ions. *Saccharomyces* is a genus of fungi that consists of various types of yeast. Copper has been used in skin care and anti-aging science because of its research findings suggest the mineral helps to rejuvenate the cells. Research indicates that the complexes found in copper are responsible for promoting cell-turnover, increasing Collagen and Elastin production, and diminishing the signs of aging. *Saccharomyces* Copper Ferment is converted into what is known as a glycopeptide using *Saccharomyces cerevisiae*. Glycopeptides have been found to inhibit cell wall synthesis. Glycopeptides have a bactericidal effect on bacteria. The *Saccharomyces cerevisiae* is utilized in products as a skin-conditioning ingredient. Research indicates that the yeast can combat oxidative stress while protecting the skin from free radical damage. Some of the benefits found in *Saccharomyces* Copper Ferment are said to include stimulation of hyaluronic acid production, retaining moisture in the skin, firming and softening the skin, repairing cell damage, anti-inflammatory activity and antioxidant activity. Copper peptides have been used in both skin and hair care products and are believed to promote growth while fighting hair loss. Copper has been used in a variety of products over the last 50 years. Early research suggests that copper peptides can bond with proteins in the body stimulate their functions. Shampoos, lotions, cosmetics, and anti-aging products have included the ingredient. Copper has also been used in sunscreens, as a skin conditioner, and to treat serious conditions such as psoriasis.

According to some embodiments, the composition or ingredients thereof, may be contained in a moisturizer or lotion. The moisturizer may include EcoG+ Liquid 100 (Silver Citrate (and) Zeolite), EnergiNius® (Fructose (and) Glycerin (and) Water (and) *Withania somnifera* Root Extract), Hydrolyzed Sodium Hyaluronate, copper ferment, lactic acid, Vitamin B3 (Niacinamide), CityStem™ (Glycerin and *Marrubium vulgare* Extract) and Sodium Hyaluronate, among other ingredients or components. In some embodiments, the moisturizer or lotion may contain some of the listed ingredients in Table 1A or 1B below or the one or more of the ingredients may be substituted with another ingredient having a similar chemical profile or effect on the skin. In some embodiments of the invention, the moisturizer further comprises a sunscreen component. The sunscreen comprises one or more mineral ingredients, such as zinc oxide. The effective weight percentage range for the one or more mineral ingredients is 13%-16%. It is understood by those skilled in the art that the amounts stated in exemplary weight percentages in Table 1A below can vary within an effective range for each of the Table 1A listed ingredients, as shown in Table 1B. Raw material names are exemplary only and may vary for the same ingredient INCI name.

TABLE 1A (Moisturizer):

| Phase | Raw Material | INCI | Exemplary Wt/Wt % |
|---|---|---|---|
| A | Deionized Water | Water | 57.75% |
| A | TeraGel | *Solanum Tuberosum* (potato) extract (and) Furcellar an | 2% |
| A | Keltrol ® CG-SFT | Xanthan Gum | 0.25% |
| A | Zemea | 1,3-Propanediol | 5% |
| A | Glycerin | Glycerin | 3% |
| A | Sisterna SP-50C | Sucrose Stearate | 1.25% |
| A | Sisterna SP-30-C | Sucrose Distearate | 1.75% |
| B | Cocoa Butter | *Theobroma Cacao* (Cocoa) Seed Butter | 8% |
| B | Sunflower Wax | *Helianthus Annuus* (Sunflower) Seed Wax | 4% |
| B | IPSol C | Coconut Alkanes | 7% |
| C | CityStem ™ | Glycerin (and) Marrubium Vulgare Extract | 2% |
| C | EnergiNius ™ | Fructose (and) Glycerin (and) Water (and) Withania somnifera Root Extract | 1% |
| C | Lactic Acid | Lactic Acid | 0.1% |
| C | Hydrolyzed Sodium Hyaluronate | Hydrolyzed Sodium Hyaluronate | 0.1% |
| C | High Molecular Weight Sodium Hyaluronate | Sodium Hyaluronate | 0.25% |
| C | Niacinamide | Niacinamide | 0.25% |
| C | IPS BIO-MIN Copper SCE | Water & Saccharomyces/Copper Ferment | 0.1% |
| C | Sonoran EO Blend (EE20-46237) | Sunflower Oil (*Helianthus Annuus* (Sunflower) Seed Oil) Lavender Oil (*Lavandula Augustifolia* (Lavender) Oil) Lemon Oil (Citrus Limon (Lemon) Peel Oil) | 1.25% |
| C | Eco G Liquid 100 | Water (Aqua) (Eau) (and) Silver Citrate (and) Zeolite | 5% |
| C | Zinc Oxide | Zinc Oxide | 13-16% (if included) |

TABLE 1B (Moisturizer):

| Phase | Raw Material | INCI | Effective Wt/Wt % Range |
|---|---|---|---|
| A | Purified Water | Water (Aqua) (Eau) | 50-70% |
| A | Zemea Propanediol | 1,3 Propanediol | 3-8% |
| A | Teragel | *Solanum Tuberosum* (Potato) Extract (and) Furcellaria Lumbricalis Extract | 1-4% |
| A | Sisterna 50C | Sucrose Stearate | 0.5-3% |
| A | Sisterna 30C | Sucrose Distearate | 0.75-3.5% |
| A | Keltrol ® CG-SFT | Xanthan Gum | 0.1-3% |
| A | Glycerin | Glycerin | 1-5% |
| B | Cocoa Butter | *Theobroma Cacao* (Cocoa) Seed Butter | 6-11% |
| B | Sunflower Wax | *Helianthus Annuus* (Sunflower) Seed Wax | 2-6% |
| B | IPSol C | Coconut Alkanes | 5-9% |
| C | IPS-Bio-Min Copper SCE | Saccharomyces/Copper Ferment (and) Water (Aqua) (Eau) (and) Sorbitan Caprylate (and) Benzoic Acid (and) 1,3 Propanediol | 0.05-1.5% |
| C | CityStem ™ | Glycerin (and) Marrubium Vulgare Extract | 1-4% |
| C | 90% Lactic Acid | Lactic Acid (and) Water (Aqua) (Eau) | 0.05-1.5% |
| C | Niacinamide USP | Niacinamide | 0.1-3% |
| C | IPS HA-ULMW | Hydrolyzed Sodium Hyaluronate | 0.1-3% |
| C | Sonoran EO Blend | *Helianthus Annuus* (Sunflower) Seed Oil (and) *Lavandula Augustifolia* (Lavender) Oil (and) Citrus Limon (Lemon) Peel Oil | 0.75-3.5% |
| C | IPS HA-HMW | Sodium Hyaluronate | 0.1-3% |
| C | ECO G 100 Liquid | Water (Aqua) (Eau) (and) Silver Citrate (and) Zeolite | 2-8% |
| C | EnergiNius ™ | Fructose (and) Glycerin (and) Water (Aqua) (Eau) (and) Withania Somnifera Root Extract | 0.5-3% |
| C | Zinc Oxide | Zinc Oxide | 13-16% |

Manufacturing the moisturizer may require a main kettle and a secondary kettle in one or more embodiments of the invention. To begin the manufacturing process, use one or more kettle(s) equipped with sweep and lightning mixing. Sweep and lightning mixing is performed using a mixer with an air powered motor or electric motor that rotates a shaft with a propeller on the end of the shaft, such as a mixer using the "Lightning" trade name.

Referring to Table 1, the manufacturing procedure for some embodiments of the moisturizer of the present invention continues as follows: add ingredients in Phase A, mixing well after each addition. Heat the main kettle to 70-75 Celsius. In the secondary kettle, add Phase B ingredients while mixing. Heat the secondary kettle to 70-75 Celsius. When both kettles have reached the proper temperature, combine Phase B into Phase A. Mix for 20 minutes. Once time is reached, cool the batch to 40-45 Celsius. Add Phase C ingredients in one by one, mixing well after each addition. Cool to 30-35 Celsius while mixing. Adjust pH with 20% Citric Acid Solution or Sodium Hydroxide to within a suitable range, such as pH 4.15-4.75.

According to an alternate embodiment of the present invention, the mixing procedure for the moisturizer or lotion may begin with adding Phase A ingredients or components, in an appropriate main vessel and mixing until homogenous at about 80 degrees Celsius (e.g., 77-83 degrees Celsius), while keeping on heat. Separately mix and heat to 80 Celsius Phase B components. With both phases at 80 Celsius, add Phase B to Phase A with vigorous mixing. Remove heat. When batch temperature is below 40 Celsius, add Phase C ingredients. Mix until homogenous. Adjust pH of the solution to within a suitable range (e.g., pH 4.15-4.75). QS [Quantum sodis] batch to 100% with enough deionized water.

According to some embodiments, the composition or ingredients thereof, may be contained in a mist. The mist may contain EcoG (Silver Citrate (and) Zeolite), Hydrolyzed Sodium Hyaluronate, copper ferment, lactic acid, Marigold (*Calendula officinalis*) Extract, allantoin, Vitamin B3 (Niacinamide), Vitamin B5 (Panthenol), sodium PCA, among other ingredients. In some embodiments, the mist may contain some of the listed ingredients or the ingredients may be substituted. It is understood by those skilled in the art that the exemplary amounts stated in weight percentages in Table 2A below can vary within an effective weight percentage range for each of the listed ingredients as shown in Table 2B below. Raw material trade names are exemplary only and may vary for the same ingredient INCI name.

TABLE 2A (Purifying Mist):

| Phase | Raw Material | INCI | Exemplary Wt/Wt % |
|---|---|---|---|
| A | Zemea Propanediol | 1,3-Propanediol | 8% |
| A | Water | Water | 74.3% |
| A | 90% Lactic Acid | Lactic Acid (and) Water (Aqua) (Eau) | 0.1% |
| B | Niacinamide USP | Niacinamide | 0.1% |
| B | Ajidew N-50 | Sodium PCA (and) Aqua | 2.5% |
| B | Panthenol | Panthenol | 0.1% |
| B | Allantoin | Allantoin | 0.1% |
| B | Suga ®Det D | Decyl Glucoside | 0.1% |
| B | AXI Calendula BL EXT | Water, Calendula Officinalis Flower Extract & Phenoxyethanol & Ethylhexylglycerin | 0.6% |
| B | IPS-ULMW HA | Hydrolyzed Hyaluronate | 0.1% |
| B | IPS Bio-Min Copper SCE | Water & Saccharomyces/Copper Ferment | 0.25% |
| C | MakiGreen LCS+ | Caprylyl/Capryl Glucoside (and) Polyglyceryl-10 Isostearate (and) Sodium Dilauramidoglutamide Lysine | 7.5% |
| C | EO Citrus Blend | *Citrus Aurantium Dulcis* (Orange) Peel Oil, *Citrus Nobilis* (Mandarin Orange) Peel Oil, *Citrus Limon* (Lemon) Peel Oil, *Citrus Grandis* (Grapefruit) Peel Oil, *Citrus Aurantium Dulcis* (Lime) Peel Oil, *Citrus Aurantium Bergamia* (Bergamot) Fruit Oil | 1.25% |
| C | EcoG+ Liquid 100 | Silver Citrate (and) Zeolite | 5% |

TABLE 2B (Purifying Mist):

| Phase | Raw Material | INCI | Effective Wt/Wt % Range |
|---|---|---|---|
| A | Purified Water | Water (Aqua) (Eau) | 65-80% |
| A | Zemea Propanediol | 1,3 Propanediol | 6-11% |
| A | 90% Lactic Acid | Lactic Acid (and) Water (Aqua) (Eau) | 0.05-0.25% |
| B | Niacinamide USP | Niacinamide | 0.05-0.25% |
| B | Protachem SPCA | Sodium PCA | 2-4% |
| B | DL-Panthenol | Panthenol | 0.05-0.25% |
| B | Allantoin | Allantoin | 0.05-0.25% |
| B | Plantaren 2000 N UP | Decyl Glucoside (and) Water (Aqua) (Eau) | 0.05-0.25% |
| B | IPS-ULMW HA | Hydrolyzed Sodium Hyaluronate | 0.05-0.25% |
| B | IPS-Bio-Min Copper SCE | Saccharomyces/Copper Ferment (and) Water (Aqua) (Eau) (and) Sorbitan Caprylate (and) Benzoic Acid (and) 1,3 Propanediol | 0.1-2.5% |
| B | AXI Calendula BL EXT | Water (Aqua) (Eau) (and) Calendula Officinalis Flower Extract (and) Phenoxyethanol (and) Ethylhexylglycerin | 0.5-2.5% |
| C | MakiGreen LCS+ | Caprylyl/Capryl Glucoside (and) Poly glyceryl-10 Isostearate (and) Sodium Dilauramidoglutamide Lysine | 5-9% |
| C | EO Citrus Blend | *Citrus Aurantium Dulcis* (Orange) Peel Oil, *Citrus Nobilis* (Mandarin Orange) Peel Oil, *Citrus Limon* (Lemon) Peel Oil, *Citrus Grandis* (Grapefruit) Peel Oil, *Citrus Aurantium Dulcis* (Lime) Peel Oil, *Citrus Aurantium Bergamia* (Bergamot) Fruit Oil | 0.5-3% |
| C | ECO G 100 Liquid | Water (Aqua) (Eau) (and) Silver Citrate (and) Zeolite | 5% |

Referring to Tables 2A or 2B, in a first step, in a main kettle equipped with sweep and lightning mixing, add water, and begin mixing.

In a second step, add the Phase A components, including Zemea Propanediol and Ritalac LA components or ingredients individually in order, and mix well after each addition until homogenous before adding the next ingredient.

In a third step, add phase B components or ingredients individually and mix well until homogenous before adding the next ingredient, in the following order: Niacinamide USP, Ajidew N-50, Panthenol, Allantoin, SugaDet D, AXI *Calendula* BL Ext, IPS-ULMW HA, and IPS Bio-Min Copper SCE.

In a fourth step, add each phase C component or ingredient individually to the main kettle, and mix well until homogeneous before adding the next ingredient, in the following order: MakiGreen LCS+, EO Citrus Blend (EE20-46239), and EcoG+100 Liquid.

In a fifth step, bring 500 g of the mixture into the lab to verify pH. Adjust the pH of the solution to 4.15-4.75 as needed with Lactic Acid, or 20% sodium hydroxide (NaOH). QS [Quantum sodis] with enough deionized Water. Finally, once the pH is within a desired range (e.g., pH 4.15-4.75), turn off all equipment, put in bottles and label. In one embodiment of the invention, the color of the purifying mist should be pale yellow, and should comprise a clear liquid with a citrus odor.

According to some embodiments, the composition or ingredients thereof, may be contained in a body lotion. The body lotion may contain EcoG+ Liquid 100, *Withania somnifera* Root Extract, Hydrolyzed Sodium Hyaluronate, copper ferment, lactic acid, allantoin, vitamin B3 (Niacinamide), vitamin B5 (Panthenol), Sodium Hyaluronate, among other ingredients. In some embodiments, the body lotion may contain some of the listed ingredients or other similar ingredients may be substituted. An exemplary list of ingredients along with an exemplary weight percentage used in embodiments of the invention is shown in Table 3A below. It is understood by those skilled in the art that the amounts stated in exemplary weight percentages in Table 3A below can vary within an effective range for each of the listed ingredients, as shown in Table 3B below. Raw material trade names are exemplary only and may vary for the same ingredient INCI name.

TABLE 3A (Body Lotion):

| Phase | Raw Material | INCI | Exemplary Wt/Wt % |
|---|---|---|---|
| A | Deionized Water | Water | 58.05% |
| A | Keltrol ® CG-SFT | Xanthan Gum | 0.2% |
| A | Teragel | Solanum Tuberosum (Potato) Pulp Extract (and) Hydrolyzed Furcellaran | 1% |
| B | Dracorin CE | Glyceryl Stearate Citrate | 2.75% |
| B | Cithrol GMS 40 SE-PA-(SG) | Glyceryl monostearate | 2.25% |
| B | Cocoa Butter | *Theobroma Cacao* (Cocoa) Seed Butter | 14% |
| B | MIGLYOL ® 812 N (F) | Capric Cappryllic Triglycerides | 8% |
| B | Sunflower Wax | *Helianthus Annuus* (Sunflower) Seed Wax | 2.5% |
| B | Behenyl Alcohol 2275 | Behenyl Alcohol | 1.7% |
| C | IPS Bio-Min Copper SCE | Water & Saccharomyces/Copper Ferment | 0.25% |
| C | Allantoin | Allantoin | 0.25% |
| C | EnergiNius ® | Fructose (and) Glycerin (and) Water (and) Withania somnifera Root Extract | 1% |
| C | Niacinamide | Niacinamide | 0.25% |
| C | Panthenol | Panthenol | 0.25% |
| C | Lactic Acid | Lactic Acid | 0.1% |

TABLE 3A-continued (Body Lotion):

| Phase | Raw Material | INCI | Exemplary Wt/Wt % |
|---|---|---|---|
| C | IPS HA-ULMW | Hydrolyzed Hyaluronic Acid | 0.1% |
| C | IPS HA-HMW | Sodium Hyaluronate | 0.1% |
| C | Spectrastat G2 N MB | Caprylhydroxamic Acid (and) Glyceryl Caprylate (and) Glycerin | 1% |
| C | EcoG+ Liquid 100 | Silver Citrate (and) Zeolite | 5% |
| C | Sonoran EO Blend (EE20-46237) | Sunflower Oil (*Helianthus Annuus* (Sunflower) Seed Oil) Lavender Oil (*Lavandula Augustifolia* (Lavender) Oil) Lemon Oil (Citrus Limon (Lemon) Peel Oil) | 1.25% |

TABLE 3B (Body Lotion):

| Phase | Raw Material | INCI | Effective Wt/Wt % Range |
|---|---|---|---|
| A | Purified Water | Water (Aqua) (Eau) | 50-70% |
| A | Teragel | Solanum Tuberosum (Potato) Extract (and) Furcellaria Lumbricalis Extract | 0.25-3% |
| A | Keltrol ® CG-SFT | Xanthan Gum | 0.1-1.5% |
| B | Dracorin CE | Glyceryl Stearate Citrate | 1-4% |
| B | Cithrol GMS 40 SE-PA-(SG) | Glyceryl Monostearate | 1-5% |
| B | Cocoa Butter | *Theobroma Cacao* (Cocoa) Seed Butter | 10-18% |
| B | Sunflower Wax | *Helianthus Annuus* (Sunflower) Seed Wax | 1-5% |
| B | Miglyol 812 N (F) | Caprylic/Capric Triglycerides | 6-14% |
| B | Behenyl Alcohol 2275 | Behenyl Alcohol | 0.5-4% |
| C | IPS-Bio-Min Copper SCE | Saccharomyces/Copper Ferment (and) Water (Aqua) (Eau) (and) Sorbitan Caprylate (and) Benzoic Acid (and) 1,3 Propanediol | 0.1-1.5% |
| C | Allantoin | Allantoin | 0.1-1.5% |
| C | 90% Lactic Acid | Lactic Acid (and) Water (Aqua) (Eau) | 0.05-1.0% |
| C | Niacinamide USP | Niacinamide | 0.1-1.5% |
| C | Panthenol | D-Panthenol | 0.1-1.5% |
| C | IPS HA-ULMW | Hydrolyzed Sodium Hyaluronate | 0.1-1.5% |
| C | Sonoran EO Blend | *Helianthus Annuus* (Sunflower) Seed Oil, *Lavendula Augustifolia* (Lavender) Oil, *Citrus Limon* (Lemon) Peel Oil | 0.75-2.5% |
| C | IPS HA-HMW | Sodium Hyaluronate | 0.1-1.5% |
| C | ECO G 100 Liquid | Water (Aqua) (Eau) (and) Silver Citrate (and) Zeolite | 3-8% |
| C | EnergiNius ® | Fructose (and) Glycerin (and) Water (Aqua) (Eau) (and) Withania Somnifera Root Extract | 0.5-3% |
| C | Spectrastat G2 N MB | Caprylhydroxamic Acid (and) Glyceryl Caprylate (and) Glycerin | 0.5-3% |

Referring to Table 3A and 3B, the procedure to create the body lotion includes using a kettle equipped with sweep and lightning mixing, add water to the main kettle and begin mixing. Add the remaining ingredients of Phase A, mixing well after each addition. Heat the main kettle to 70-75 Celsius. In the secondary kettle, add Phase B while mixing. Heat the secondary kettle to 70-75 Celsius. When both kettles have reached the proper temperature, combine Phase B into Phase A and mix for 20 minutes. Once time is reached, cool the batch to 40-45 degrees Celsius. Add the ingredients of Phase C, mixing well after each addition. Cool to 30-35 degrees Celsius while mixing. Adjust pH with 20% solution of Citric Acid or Sodium Hydroxide to pH 5.5-6.0.

According to some embodiments, the procedure to create the body lotion includes adding Phase A in a suitable container, mixing until homogenous, and heating to 75 degrees Celsius while mixing. In a separate container, add Phase B and heat to 75 degrees Celsius by mixing. Once both phases have reached 75 degrees Celsius and are homogenous, add Phase B into phase A while mixing. Mix until homogenous and remove heat. Cool to below 40 degrees Celsius. Add Phase C ingredients or components. Adjust the pH of the solution to 5.5-6.0 using 20% Citric Acid and 20% NaOH. QS [Quantum sodis] with enough deionized water.

According to some embodiments, the composition or ingredients thereof may be contained in a serum, wherein the serum comprises a probiotic night serum with the exemplary ingredients list shown in Tables 4A and 4B below. It is understood by those skilled in the art that the amounts stated in weight percentages in Table 4A herein can vary within an effective range for each of the listed ingredients as shown in Table 4B below. Raw material trade names are exemplary only and may vary for the same ingredient INCI name.

TABLE 4A (Probiotic Night Serum):

| Phase | Raw Material | INCI | Exemplary Wt/Wt % |
|---|---|---|---|
| 3 | Zemea Propanediol | Propanediol | 15.000% |
| P2 | Glycerin | Glycerin | 2.000% |
| 4 | Betaine Anhydrous | Betaine | 0.200% |
| P2 | Vanzan NF | Xanthan Gum | 1.000% |
| 1 | Distilled Water | Water | 72.05% |
| 5 | Ajidew ® N-50 | Sodium PGA (and) Aqua | 2.000% |
| 6 | Allantoin | Allantoin | 0.250% |
| 7 | ESP Vegabead ProS | Hansenula/Kloeckera/ Lactobacillus/Lactococcus/ Leuconostoc/, Pediococcus/Saccharomyces /Fig/Lemon Ferment Sorbitan Oleate/ Cellulose Gum Chitosan, Citric Acid, Water, Glycerin Isoeicosane | 2.000% |
| 8 | Synchrolife | Glycerin, Pentylene Glycol, Rosmarinus Officinalis (Rosemary Leaf) Extract, Palmitoyl Tetrapeptide-7, (and) Chrysin | 2.000 % |
| P9 | Makigreen LCS+ | Caprylyl/Capryl Glucoside (and) Polyglyceryl-10 Isostearate (and) Sodium Dilauramidoglutamide Lysine | 2.000 % |
| P9 | Lavender & Lemongrass EO Blend | Sunflower Oil (*Helianthus Annuus* (Sunflower) Seed Oil), Lavender Oil (*Lavandula Angustifolia* (Lavender) Oil), Lemongrass Oil | 0.500 % |

TABLE 4A-continued (Probiotic Night Serum):

| Phase | Raw Material | INCI | Exemplary Wt/Wt % |
|---|---|---|---|
| 10 | Spectrastat G2 N MB | (*Cymbopogon Schoenanthus* Oil) Caprylhydroxamic Acid (and) Glyceryl Caprylate (and) Glycerin | 1.000 % |
| | | | 97.95 % |

TABLE 4B (Probiotic Night Serum):

| Phase | Raw material | INCI | Effective Wt/Wt % Range |
|---|---|---|---|
| 1 | Purified Water | Water (Aqua) (Eau) | 65-85% |
| P2 | Glycerin | Glycerin | 0.5-3% |
| P2 | Vanzan NF | Xanthan Gum | 0.5-4% |
| 3 | Zemea Propanediol | 1,3 Propanediol | 12-18% |
| 4 | Betaine Anhydrous | Betaine | 0.1-2.5% |
| 5 | Protachem SPCA | Sodium PCA | 1-5% |
| 6 | Allantoin | Allantoin | 0.1-3% |
| 7 | ESP Vegabead Pro S | Water (Aqua) (Eau) (and) Glycerin (and) Isoeicosane (and) Hansenula/Kloeckera/ Lactobacillus/Lactococcus/ Leuconostoc/Pediococcus/ Saccharomyces/Fig/Lemon Ferment (and) Sorbitan Oleate (and) Cellulose Gum (and) Chitosan (and) Citric Acid | 0.5-4% |
| 8 | Synchrolife | Glycerin (and) Pentylene Glycol (and) *Rosmarinus Officinalis* (Rosemary Leaf) Extract (and) Palmitoyl Tetrapeptide-7 (and) Chrysin | 0.5-4% |
| P9 | MakiGreen LCS+ | Caprylyl/Capryl Glucoside (and) Polyglyceryl-10 Isostearate (and) Sodium Dilauramidoglutamide Lysine | 1-4% |
| P9 | EO Blend Lavender & Lemongrass #EE21-47336 | *Helianthus Annuus* (Sunflower) Seed Oil, *Lavandula Angustifolia* (Lavender) Oil, *Cybopogon Shoenanthus* (Lemongrass) Oil | 0.1-1.5% |
| 10 | Spectrostat G2 N MB | Caprylhydroxamic Acid (and) Glyceryl Caprylate (and) Glycerin | 0.5-3% |

Referring to Table 4, according to some embodiments, the procedure to create the serum includes:

A first step of: In a main kettle equipped with sweep and lightning mixing, add water and begin mixing.

Second: In a separate suitable vessel, premix the following materials: Glycerin and Vanzan NF. When completely uniform, slowly add this mixture to the main kettle.

Third, Add the following in order to the main kettle, mixing well after each addition: Zemea Propanediol and Betaine Anhydrous. Mix 10 minutes for uniformity.

Fourth, add the following in order, mixing well after each addition: Sodium PCA, Allantoin, ESP Vegabead ProS, Synchrolife.

Fifth, in a separate suitable vessel, premix the following materials: Makigreen LCS+ and Lavender & Lemongrass EO EE21-47336. When completely uniform, slowly add to the main kettle. Mix at least 15 minutes until uniform.

Sixth, add the following material to the main kettle: Spectrostat G2N MB. Mix at least 15 minutes until uniform.

Seventh, take 500 g to perform a pH check. The main kettle mixture should be pH tested to within a range of 6.25-6.75 pH inclusive, using Lactic Acid and/or 20% sodium hydroxide to adjust pH as needed. Finally, once the pH is within a desired range, put in containers and label.

According to some embodiments, the composition or ingredients thereof, may be contained in a probiotic serum. The probiotic serum may contain propandiol, glycerin, betaine, xanthan gum, distilled water, sodium PCA, Allantoin, ESP Vegabead ProS (e.g., as manufactured by Earth Supply Products; comprising *Hansenula, Kloeckera, Lactobacillus, Lactococcus, Leuconostoc, Pediococcus, Saccharomyces*, Fig, Lemon Ferment, Sorbitan Oleate, Cellulose Gum, Chitosan Citric Acid, Water, Glycerin, and Isoeicosane), Synchrolife™ (e.g., as manufactured by Corda (Sederma); comprising glycerin, pentylene glycol, rosemary leaf extract, palmitoyl tetrapeptide-7, and chrysin), Makigreen LCS+(e.g., as manufactured by KOBO; comprising caprylyl/capryl glucoside, polyglyceryl-10 isostearate, and sodium dilauramidoglutamide lysine), Lavender and Lemongrass essential oil blend (e.g., as manufactured by Premier Specialties), and Spectrastat G2N MB (e.g., as manufactured by Inolex; comprising caprylhydroxamic acid, glyceryl caprylate, and glycerin), among other ingredients. In some embodiments, the probiotic serum may comprise a probiotic night serum that may be applied after cleansing the skin in the evening prior to bedtime. In one or more embodiments of the invention, the probiotic night serum may contain some of the listed ingredients, or one or more of the ingredients may be substituted.

According to some embodiments, the composition or ingredients thereof may be contained in a cleanser, wherein the cleanser comprises a prebiotic-based low-foaming cleanser with the exemplary ingredients list shown in Table 5 below. It is understood by those skilled in the art that the amounts stated in weight percentages can vary within an effective range for each of the listed ingredients, as shown in Table 5 below. Raw material trade names are exemplary only and may vary for the same ingredient INCI name.

TABLE 5

(Prebiotic-based Low-Foaming Cleanser):

| Phase | Ingredient Trade Name (Raw Material) | INCI Name | Wt/Wt % Range |
|---|---|---|---|
| A | Purified Water | Water (Aqua) (Eau) | 65-85% |
| A | Zemea Propanediol | 1,3 Propanediol | 12-18% |
| A | Glycerin USP | Glycerin | 0.5-3% |
| A | IPS-HA-ULMW | Hydrolyzed Sodium Hyaluronate | 0.05-1.5% |
| A | Vanzan NF | Xanthan Gum | 0.5-4% |
| A | Pureact I-78 Flakes | Sodium Cocoyl Isethionate | 3-7% |
| B | Stearyl Alcohol | Stearyl Alcohol | 3-9% |
| B | Cetyl Alcohol | Cetyl Alcohol | 3-9% |
| C | Niacinamide | Niacinamide | 0.05-1.5% |
| C | Panthenol | D-Panthenol | 0.05-1.5% |
| C | 90% Lactic Acid | Lactic Acid | 0.05-1.5% |
| C | ColaDet KC-40 | Potassium Cocoate | 12-18% |
| C | Ecodermine ™ | Glycerin (and) Lactitol (and) Xylitol | 0.5-4% |
| C | Sonoran EO Blend EE21-48993 | *Prunus Amygdalus Dulcis* (Sweet Almond) Oil, *Citrus Aurantium Dulcis* (Orange) Flower Extract, *Citrus Aurantium Dulcis* (Orange) Peel Oil, *Citrus Aurantium Bergamia* (Bergamot) Fruit Oil, *Citrus Nobilis* (Mandarin Orange) Peel Oil, *Pogostemon Cablin* (Patchouli) Oil, *Amyris Balsamifera* (Amyris) Bark Oil, Citrus Limon (Lemon) Peel Oil | 0.75-3.5% |
| C | Spectrostat G2 N MB | Caprylhydroxamic Acid (and) Glyceryl Caprylate (and) Glycerin | 0.5-3% |

Referring to Table 5, according to some embodiments, the procedure to create the prebiotic creamy cleanser comprises:

A first step of: In a main kettle equipped with heating capabilities and sweep and lightning mixing, add water and begin mixing.

Second: In the main kettle, add the following in order, mixing well after each addition: Glycerin, Zemea Propanediol, IPS-HA-ULMW, Vanzan NF (Xanthan Gum), and Pureact I-78-Flake.

Third, Heat the main kettle to 70-75 degrees Celsius.

Fourth, while maintaining temperature, add the following ingredients to the main kettle in order, mixing well after each addition: Stearyl Alcohol and Cetyl Alcohol. Mix at least 20 minutes until completely uniform.

Fifth, when completely uniform, cool the batch to 35-40 degrees Celsius.

Sixth, add the following in order, mixing well after each addition: ColaDet KC-40, Niacinamide, Panthenol, Lactic Acid, Ecodermine, Spectrastat G2 N MB, Sonoran EO Blend EE21-48993.

Seventh, take 500 g to perform a pH check. The main kettle mixture should be pH tested to within a range of 5.5-6.0 pH inclusive, using Lactic Acid and/or 20% sodium hydroxide to adjust pH as needed. Finally, once the pH is within a desired range, turn off all equipment and put in containers and label.

According to some embodiments, the skin treatment includes using the cleanser to cleanse the skin and prepare the skin for the next steps of the treatment. As a next step, the lotion or moisturizer described above is applied to the skin. The first two steps are typically performed at the beginning of the day. As a next step, and potentially multiple times a day, the purifying or inoculating mist described above is misted over the skin. As a next step, at the end of the day, or before bedtime, a cleanser is used to cleanse the skin. As a final step, a night serum described above is applied to the skin.

Additional information and suppliers of the above-listed ingredients (and the corresponding trade names) can be found in the International Cosmetic Ingredient Dictionary and Handbook, 16th Edition (2016), which is incorporated herein by reference in its entirety. INCI (International Nomenclature of Cosmetic Ingredients) is designed to help cosmetic formulators find information on cosmetics ingredients. INCI names (International Nomenclature Cosmetic Ingredient) are systematic names internationally recognized to identify cosmetic ingredients (i.e., plant extracts, oils, chemicals). For example, EU, USA, China, Japan and Canada may only accept INCI names for cosmetic product labelling. As an example, INCI names may be used for cosmetic labeling instead of using chemical names because a cosmetic ingredient can have various chemical names (IUPAC name, common name, CAS name, etc.) in different countries. The use of harmonized INCI names can minimize confusion.

Further, the extracts identified above can be produced by extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc. Extracts may be produced in some embodiments of the invention by obtaining the corresponding fruit, seed, or leaf, to produce the extract by extraction methods which are known to those of ordinary skill in the art. In addition, a person of ordinary skill in the art would be able to isolate any one of the extracts identified above from parts of the corresponding plant by using any suitable method known in the art. In one non-limiting example, the plant (or any part of the plant such as the leaves, stems, bark, roots, fruit, flowers or flower buds, seeds, seed pods, sap, whole plant, etc.) can be disrupted by mechanical means which results in a puree. The puree is then processed to be substantially free of impurities or undesired solids. The puree can then be poured into a shallow vessel and quickly exposed to a low temperature, e.g., flash frozen, for example at −20 degrees Celsius or lower, under a vacuum for removal of water content. The resultant extract can then be used in the compositions of the present invention. In other aspects, aqueous, alcoholic or oil-based extraction techniques, or combinations thereof, can be used on the whole plant or any part thereof to produce an extract. In such a process, the desired part of the plant or the whole plant is crushed up (e.g., blender) and then subjected to a desired solvent (e.g., water, alcohol, water/alcohol, or oil-based solvents) to obtain the desired extract. The extract can then be stored in liquid form, lyophilized, or subjected to further processing techniques (e.g., heating, cooling, etc.). Extraction processes are known to those of ordinary skill in the art (e.g., maceration, infusion, percolation, digestion, decoction, hot continuous extraction, aqueous-alcoholic extract, counter current extract, microwave assisted extraction ultrasound extraction, supercritical fluid extracts, phytonic extract (e.g., with hydro-fluoro-carbon solvents), etc.

Essential oils include oils derived from herbs, flowers, trees and other plants. Such oils are typically present as tiny droplets between the plant's cells, and can be extracted by several methods known to those of skill in the art (e.g., steam distilled, enfleurage (e.g., extraction by using fat, maceration, solvent extraction, or mechanical pressing). When these types of oil are exposed to air they tend to evaporate (e.g., a volatile oil). As a result, many essential oils are colorless, but with age they can oxidize and become darker, Essential oils are insoluble in water and are soluble in alcohol, ether, fixed oils (vegetal), and other organic solvents. Typical physical characteristics found in essential oils include boiling points that vary from about 160 degrees to 240 degrees Celsius. Essential oils typically are named by the plant from which the oil is found. Non-limiting examples of essential oils that can be used in embodiments of the present invention include lavender oil, lemon oil, lemon peel oil, lime oil, mandarin oil, orange oil, and grapefruit oil.

Other essential oils known to those skilled in the art are also contemplated as being useful as active ingredients in some embodiments of the present invention.

Thickening agents, including thickener or gelling agents, include substances which can increase the viscosity and/or stability of a composition in one or more embodiments of the present invention without substantially modifying the efficacy of the active ingredient within the composition. Non-limiting examples of thickening agents that may be used in embodiments of the present invention include gums such as xanthan gum, acacia, agar, guar gum, hyaluronic acid, kelp, locust bean gum, natto gum, and/or mixtures thereof.

It is also contemplated that the products and compositions of some embodiments of the present invention can include one or more effective amounts of the ingredients discussed in this specification. The compositions can also include any number of combinations of additional ingredients described in this specification (e.g., additional cosmetic or pharmaceutical ingredients). Furthermore, the concentrations of any ingredient within the compositions or products are within the ranges specified as above in one or more embodiments of the present invention. In non-limiting aspects of embodiments of the present invention, the percentage can be calculated by wet weight of the total composition. A person of ordinary skill in the art would understand that concentrations of each ingredient in the product or composition of embodiments of the present invention disclosed herein can vary depending on the addition, substitution, and/or subtraction of ingredients in a given composition.

The products or compositions of some embodiments of the present invention disclosed herein may include or be incorporated into several types of vehicles and carriers. The vehicle or carrier may comprise a pharmaceutically or dermatologically acceptable or beneficial vehicle or carrier. Non-limiting examples of vehicles or carriers include water, glycerin, alcohol, oil, a silicon-containing compound, a silicone compound, and wax. Variations and other appropriate vehicles will be apparent to the persons skilled in the art and are appropriate for use in embodiments of the present invention. In certain aspects known to those skilled in the art, the concentrations and combinations of the compounds, ingredients, and agents can be selected in such a way that the combinations are chemically compatible and do not form complexes which precipitate from the finished product.

The compositions of embodiments of the present invention disclosed in this specification can be structured or formulated into a variety of different forms. Non-limiting examples include creams, lotions, solutions (both aqueous and hydro-alcoholic), gels, ointments, emulsions (e.g., water-in-oil, water-in-oil-in water, oil-in-water, silicone-in-water, oil-in-water-in-oil, oil-in-water-in-silicone emulsions), masks, peels, and anhydrous bases (such as lipsticks, lip balms, lip salves, and powders). Variations and other structures will be apparent to those skilled in the art and are appropriate for use in embodiments of the present invention disclosed herein.

The skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active or any other ingredients, compositions, or methods, and in the steps or in the sequence of steps of the method described herein without departing from the concept, spirit, and scope of the invention. More specifically, it is understood by persons of ordinary skill in the art that certain ingredients which are chemically and/or physiologically related may be substituted for one or more related ingredients in embodiments of the present invention described herein while the same or similar results would be achieved. All such similar substitutes and/or modifications are deemed to be within the spirit, scope and concept of embodiments of the present invention described in this specification and the appended claims.

Kits are also contemplated as being used in certain aspects of the present invention. For instance, compositions of some embodiments of the present invention described herein can be included in a kit. A kit may include all or some of the products to be used in a daily skin treatment. The products may be dispensed in any of a variety of possible containers, e.g., a glass or plastic bottle, a metal tube, a laminate tube, a plastic tube, a pressurized container, a barrier container, a package, a biodegradable package, a compostable package, a recyclable package, a compartment, a lipstick container, a lip balm container, a glass jar, a plastic jar, a compact container, cosmetic pans that can hold cosmetic compositions, or other types of containers. The containers can dispense a pre-determined or variable amount of the composition in one or more embodiments of the present invention described herein. In one embodiment of the invention, the container can be squeezed (e.g., such as a metal, laminate, or plastic tube) to dispense a desired amount of the composition. In other embodiments, the composition may be dispensed as a spray, an aerosol, a liquid, a fluid, a lotion, or a semi-solid. A kit may also comprise instructions for using, applying, maintaining, an/or storing the compositions of one or more embodiments of the present invention included as components of the kit.

Additional Exemplary Embodiments

A first skincare composition embodiment comprising an antimicrobial component, an antiaging component and a moisturizing component comprising at least one alpha-hydroxy acid.

The first skincare composition embodiment, wherein the antimicrobial component comprises silver citrate and zeolite blend.

The first skincare composition embodiment also according to the previous paragraph, wherein the zeolite blend is at 5% relative to total weight of the composition.

The first skincare composition embodiment, wherein the antiaging component comprises at least one hydrolyzed sodium hyaluronate.

The first skincare composition embodiment, further comprising an antioxidant component.

The first skincare composition embodiment, further comprising a vitamin component.

The first skincare composition embodiment, further comprising at least one copper ferment.

The first skincare composition embodiment, wherein the alpha-hydroxy acid comprises at least one of lactic acid, tartaric acid, citric acid, malic acid, glycolic acid, gluconic, and salicylic acid.

The first skincare composition embodiment, further comprising a screen-emitted artificial visible light protecting component.

The first skincare composition embodiment according to the previous paragraph, wherein the screen-emitted artificial visible light protecting component comprises at least one of *Withania somnifera* root extract, Marigold (*Calendula officinalis*) Extract, PEPHA®-AGE, and niacinamide.

The first skincare composition embodiment, wherein the antimicrobial component comprises at least one or more of: Hypochlorous Acid, Oregano, Benzochloride, Aloe Vera, Peppermint Extract, Rosemary Extract, Ginger, Manuka Honey, Tea Tree Oil, *Coleus forskohlii* root oil, *Kaempferia galanga* root extract, *Olea europaea* leaf extract, *Curcuma longa*, Zeolite, *Melia azadirachta*, *Camellia sinensis* leaf extract, Silver, and Colloidal Silver.

The first skincare composition embodiment, wherein the antiaging component comprises at least one or more of: *Dracaena cambodiana* Leaf Extract (Dragons Blood), *Saccharomyces* Copper Ferment, Acetyl hexapeptide 3, Acetyl hexapeptide 8, Acetyl hexapeptide 20, Palmitoyl pentapeptide, Palmitoyl oligopeptide, Tripeptide 1, Acetyl tetrapeptide-9, Vitamin C, Vitamin A, Vitamin E, Resveratrol, Coenzymeq10, Niacinamide, Polyphenols, Flavonoids, Glutathione, Peony Extract, Malachite Extract, Hydrolyzed Sodium Hyaluronate, and Hydrolyzed Hyaluronate.

The first skincare composition embodiment, wherein the moisturizing component comprises at least one or more of: Lactic Acid, Tartaric Acid, Citric Acid, Malic Acid, Glycolic Acid, Gluconic Acid, and Salicylic Acid.

The first skincare composition embodiment, wherein the screen-emitted artificial visible light protecting component comprises at least one or more of: Marigold (*Calendula officinalis*) Extract, EnergiNius® (Fructose (and) Glycerin (and) Water (and) *Withania somnifera* Root Extract), PEPHA®-AGE, and Vitamin B3.

A first treatment method for improving skin by administering to an area in need thereof a composition comprising an effective amount of an antimicrobial component, an antiaging component and a moisturizing component comprising at least one alpha-hydroxy acid.

A second treatment method for improving skin by administering to an area in need thereof multiple compositions, the method comprising:
(1) cleaning the area with a cleanser composition comprising at least one of Ecodermine™ (glycerin, lactitol, and xylitol), lactic acid, vitamin B3, and vitamin B5;
(2) moisturizing the area with a lotion composition comprising at least one of EcoG, EnergiNius® (Fructose (and) Glycerin (and) Water (and) *Withania somnifera* Root Extract), Hydrolyzed Sodium Hyaluronate, copper ferment, lactic acid, Vitamin B3 (Niacinamide), CityStem® (Glycerin and *Marrubium vulgare* Extract) and Sodium Hyaluronate;
(3) misting the skin with a misting composition comprising at least one of ecoG, Hydrolyzed Sodium Hyaluronate, copper ferment, lactic acid, Marigold (*Calendula officinalis*) Extract, allantoin, Vitamin B3 (Niacinamide), Vitamin B5 (Panthenol), sodium PCA;
(4) cleaning the area with the cleanser; and applying a night serum composition to the area, the night serum comprising at least one of propandiol, glycerin, betaine, xanthan gum, distilled water, sodium PCA, Allantoin, ESP Vegabead ProS (*Hansenula, Kloeckera, Lactobacillus, Lactococcus, Leuconostoc, Pediococcus, Saccharomyces*, Fig, Lemon Ferment, Sorbitan Oleate, Cellulose Gum, Chitosan Citric Acid, Water, Glycerin, and Isoeicosane), Synchrolife™ (glycerin, pentylene glycol, rosemary leaf extract, palmitoyl tetrapeptide-7, and chrysin), Makigreen LCS+(caprylyl/capryl glucoside, polyglyceryl-10 isostearate, and sodium dilauramidoglutamide lysine), Lavender and Lemongrass essential oil blend, and Spectrastat G2N MB (caprylhydroxamic acid, glyceryl caprylate, and glycerin).

A second composition embodiment comprising:
(1) at least one alpha hydroxy acid selected from the group consisting of lactic acid, citric acid, tartaric acid, citric acid, malic acid, glycolic acid, gluconic acid, salicylic acid and mixtures thereof;
(2) at least one blue light mitigator selected from the group consisting of *Withania somnifera* root extract, Marigold (*Calendula officinalis*) Extract, *Scenedesmus rubescens* extract, and niacinamide PC;
(3) at least one hyaluronic acid selected from the group consisting of hydrolyzed sodium hyaluronate, hydrolyzed hyaluronic acid, sodium acetylated hyaluronate, and sodium hyaluronate;
(4) at least one antioxidant selected from the group consisting of *saccharomyces* copper ferment; and
(5) at least one silver zeolite.

The second composition embodiment, further comprising ingredients selected from a group consisting of: a mixture of lactitol and xylitol with glycerin (Ecodermine™, Marigold (*Calendula officinalis*) Extract, allantoin, niacinamide, panthenol, hyaluronic acid, prebiotics, probiotics, *Marrubium vulgare* extract (Citystem®), sodium PCA, sodium hyaluronate, hydrolyzed hyaluronate, a mixture of glycerin and pentylene glycol and *Rosmarinus officinalis* (Rosemary) leaf extract and palmitoyl tetrapeptide-7 with chrysin (Synchrolife™), and combinations thereof.

A third skincare composition embodiment comprising:
an antimicrobial component including silver citrate and zeolite blend;
an antiaging component comprising copper ferment;
a moisturizing component comprising hydrolyzed sodium hyaluronate; and
a screen-emitted artificial visible light protection component comprising *Withania somnifera* root extract.

The third skincare composition embodiment, further comprising lactic acid.

A first skincare formulation prepared by adding an antimicrobial component, an antiaging component, and a moisturizing component comprising at least one alpha-hydroxy acid.

The first skincare formulation prepared according to the previous paragraph, wherein the antimicrobial component comprises silver citrate and zeolite blend.

The first skincare formulation prepared according to the previous paragraph, wherein the zeolite blend is at 5% relative to total weight of the composition.

The first skincare formulation, wherein the antiaging component comprises at least one hydrolyzed sodium hyaluronate.

The first skincare formulation, further adding an antioxidant component.

The first skincare formulation, further adding a vitamin component.

The first skincare formulation, further adding at least one copper ferment.

The first skincare formulation, wherein the alpha-hydroxy acid comprises at least one of lactic acid, tartaric acid, citric acid, malic acid, glycolic acid, gluconic, and salicylic acid.

The first skincare formulation, further adding a screen-emitted artificial visible light protecting component.

The first skincare formulation prepared according to the previous paragraph, wherein the screen-emitted artificial visible light protecting component comprises at least one of *Withania somnifera* root extract, Marigold (*Calendula officinalis*) Extract, PEPHA®-AGE, and niacinamide.

The first skincare formulation, wherein the antimicrobial component comprises at least one or more of: Hypochlorous Acid, Oregano, Benzochloride, Aloe Vera, Peppermint Extract, Rosemary Extract, Ginger, Manuka Honey, Tea Tree Oil, *Coleus forskohlii* root oil, *Kaempferia galanga* root extract, *Olea europaea* leaf extract, *Curcuma longa*, Zeolite, *Melia azadirachta, Camellia sinensis* leaf extract, Silver, and Colloidal Silver.

The first skincare formulation, wherein the antiaging component comprises at least one or more of: *Dracaena cambodiana* Leaf Extract (Dragons Blood), *Saccharomyces* copper ferment, Acetyl hexapeptide 3, Acetyl hexapeptide 8, Acetyl hexapeptide 20, Palmitoyl pentapeptide, Palmitoyl oligopeptide, Tripeptide 1, Acetyl tetrapeptide-9, Vitamin C, Vitamin A, Vitamin E, Resveratrol, Coenzymeq10, Niacinamide, Polyphenols, Flavonoids, Glutathione, Peony Extract, Malachite Extract, Hydrolyzed Sodium Hyaluronate, and Hydrolyzed Hyaluronate.

The first skincare formulation, wherein the moisturizing component comprises at least one or more of: Lactic Acid, Tartaric Acid, Citric Acid, Malic Acid, Glycolic Acid, Gluconic Acid, and Salicylic Acid.

The first skincare formulation, wherein the screen-emitted artificial visible light protecting component comprises at least one or more of: Marigold (*Calendula officinalis*) Extract, EnergiNius®, PEPHA®-AGE, and Vitamin B3.

A third treatment method for improving skin by administering to an area in need thereof a skincare formulation prepared by adding an effective amount of an antimicrobial component, an antiaging component and a moisturizing component comprising at least one alpha-hydroxy acid.

A fourth treatment method for improving skin by administering to an area in need thereof multiple skincare formulations, the method comprising:
(1) cleaning the area with a cleanser formulation prepared by adding at least one of Ecodermine™ (glycerin, lactitol, and xylitol), lactic acid, vitamin B3, and vitamin B5;
(2) moisturizing the area with a lotion formulation prepared by adding at least one of EcoG, EnergiNius® (Fructose (and) Glycerin (and) Water (and) *Withania somnifera* Root Extract), Hydrolyzed Sodium Hyaluronate, copper ferment, lactic acid, Vitamin B3 (Niacinamide), CityStem® (Glycerin and *Marrubium vulgare* Extract) and Sodium Hyaluronate;
(3) misting the skin with a misting formulation prepared by adding at least one of EcoG, Hydrolyzed Sodium Hyaluronate, copper ferment, lactic acid, Marigold (*Calendula officinalis*) Extract, allantoin, Vitamin B3 (Niacinamide), Vitamin B5 (Panthenol), and sodium PCA;
(4) cleaning the area with the cleanser formulation; and
(5) applying a night serum formulation to the area, the night serum formulation prepared by adding at least one of propandiol, glycerin, betaine, xanthan gum, distilled water, sodium PCA, Allantoin, ESP Vegabead ProS (*Hansenula, Kloeckera, Lactobacillus, Lactococcus, Leuconostoc, Pediococcus, Saccharomyces*, Fig, Lemon Ferment, Sorbitan Oleate, Cellulose Gum, Chitosan, Citric Acid, Water, Glycerin, and Isoeicosane), Synchrolife™ (glycerin, pentylene glycol, rosemary leaf extract, palmitoyl tetrapeptide-7, and chrysin), Makigreen LCS+(caprylyl/capryl glucoside, polyglyceryl-10 isostearate, and sodium dilauramidoglutamide lysine), Lavender and Lemongrass essential oil blend, and Spectrastat G2N MB (caprylhydroxamic acid, glyceryl caprylate, and glycerin).

A second skincare formulation prepared by combining:
(1) at least one alpha hydroxy acid selected from the group consisting of lactic acid, citric acid, tartaric acid, citric acid, malic acid, glycolic acid, gluconic acid, salicylic acid and mixtures thereof;
(2) at least one blue light mitigator selected from the group consisting of *Withania somnifera* root extract, Marigold (*Calendula officinalis*) Extract, *Scenedesmus rubescens* extract, and niacinamide PC;
(3) at least one hyaluronic acid selected from the group consisting of hydrolyzed sodium hyaluronate, hydrolyzed hyaluronic acid, sodium acetylated hyaluronate, and sodium hyaluronate;
(4) at least one antioxidant selected from the group consisting of *saccharomyces* copper ferment; and
(5) at least one silver zeolite.

The second skincare formulation, further adding one or more ingredients selected from a group consisting of: a mixture of lactitol and xylitol with glycerin (Ecodermine™, Marigold (*Calendula officinalis*) Extract, allantoin, niacinamide, panthenol, hyaluronic acid, prebiotics, probiotics, *Marrubium vulgare* extract (Citystem®), sodium PCA, sodium hyaluronate, hydrolyzed hyaluronate, a mixture of glycerin and pentylene glycol and *Rosmarinus officinalis* (Rosemary) leaf extract and palmitoyl tetrapeptide-7 with chrysin (Synchrolife™), and combinations thereof.

A third skincare formulation prepared by combining:
(1) an antimicrobial component including silver citrate and zeolite blend;
(2) an antiaging component comprising *Saccharomyces* copper ferment;
(3) a moisturizing component comprising hydrolyzed sodium hyaluronate; and
(4) a screen-emitted artificial visible light protection component comprising *Withania somnifera* root extract.

The third skincare formulation prepared as above, and further adding lactic acid.

While the present invention has been particularly described with respect to the embodiments, it will be appreciated that various alterations, modifications and adaptations may be made based on the present disclosure and are intended to be within the scope of the present invention. While the invention has been described in connection with what are presently considered to be the most practical and preferred embodiments, it is to be understood that the present invention is not limited to the disclosed embodiments but, on the contrary, is intended to cover various modifications and equivalent arrangements included within the scope of the appended claims

What is claimed is:

1. A skincare composition comprising an antimicrobial component, an antiaging component, a screen-emitted artificial visible light protecting component comprising at least one of *Withania somnifera* root extract or *Scenedesmus rubescens* extract, and a moisturizing component comprising at least one alpha-hydroxy acid.

2. The skincare composition according to claim 1, wherein the antimicrobial component comprises silver citrate and zeolite blend.

3. The skincare composition according to claim 2, wherein the zeolite blend is at 5% relative to total net weight of the composition.

4. The skincare composition according to claim 1, wherein the antiaging component comprises at least one hydrolyzed sodium hyaluronate.

5. The skincare composition according to claim 1, further comprising an antioxidant component.

6. The skincare composition according to claim 1, further comprising a vitamin component.

7. The skincare composition according to claim 1, further comprising at least one copper ferment.

8. The skincare composition according to claim 1, wherein the alpha-hydroxy acid comprises at least one of lactic acid, tartaric acid, citric acid, malic acid, glycolic acid, gluconic acid, and salicylic acid.

9. The skincare composition according to claim 1, wherein the antimicrobial component comprises at least one or more of: hypochlorous acid, oregano, benzalkonium chloride, aloe vera, peppermint extract, rosemary extract, ginger, Manuka honey, tea tree oil, *Coleus forskohlii* root oil, *Kaempferia galanga* root extract, *Olea europaea* leaf extract, *Curcuma longa*, zeolite, *Melia azadirachta*, *Camellia sinensis* leaf extract, silver, and colloidal silver.

10. The skincare composition according to claim 1, wherein the antiaging component comprises at least one or more of: *Dracaena cambodiana* leaf extract, *Saccharomyces* copper ferment, acetyl hexapeptide-3, acetyl hexapeptide-8, acetyl hexapeptide-20, palmitoyl pentapeptide, palmitoyl oligopeptide, tripeptide-1, actyl tetrapeptide-9, vitamin C, vitamin A, vitamin E, reservatrol, coenzyme $Q_{10}$, niacinamide, polyphenols, flavonoids, glutathione, peony extract, malachite extract, hydrolyzed sodium hyaluronate, and hydrolyzed hyaluronate.

11. The skincare composition according to claim 1, wherein the moisturizing component comprises at least one or more of: lactic acid, tartaric acid, citric acid, malic acid, glycolic acid, gluconic acid, and salicylic acid.

12. The skincare composition according to claim 1, wherein the screen-emitted artificial visible light protecting component further comprises at least one or more of: *Calendula officinalis* extract; a mixture comprising fructose, glycerin, water, and *Withania somnifera* root extract; and vitamin B3.

13. A composition comprising:
at least one alpha hydroxy acid selected from the group consisting of lactic acid, citric acid, tartaric acid, malic acid, glycolic acid, gluconic acid, salicylic acid and mixtures thereof;
at least one blue light mitigator selected from the group consisting of *Withania somnifera* root extract, *Calendula officinalis* extract, *Scenedesmus rubescens* extract, and niacinamide;
at least one hyaluronic acid selected from the group consisting of hydrolyzed sodium hyaluronate, hydrolyzed hyaluronic acid, sodium acetylated hyaluronate, and sodium hyaluronate;
at least one antioxidant selected from the group consisting of *Saccharomyces* copper ferment; and
at least one composition comprising silver citrate and zeolite blend.

14. The composition according to claim 13, further comprising ingredients selected from a group consisting of: a mixture of lactitol and xylitol with glycerin, *Calendula officinalis* extract, allantoin, niacinamide, panthenol, hyaluronic acid, prebiotics, probiotics, *Marrubium vulgare* extract, sodium PCA, sodium hyaluronate, hydrolyzed hyaluronate, a mixture of glycerin and pentylene glycol and *Rosmarinus officinalis* (rosemary) leaf extract and palmitoyl tetrapeptide-7 with chrysin, and combinations thereof.

15. A skincare composition comprising:
an antimicrobial component including silver citrate and zeolite blend;
an antiaging component comprising copper ferment;

a moisturizing component comprising hydrolyzed sodium hyaluronate; and a screen-emitted artificial visible light protection component comprising at least one of *Scenedesmus rubescens* extract and *Withania somnifera* root extract.

16. The skincare composition of claim 15, further comprising lactic acid.

17. A skincare formulation prepared by adding an antimicrobial component, an antiaging component, a screen-emitted artificial visible light protecting component comprising at least one of *Withania somnifera* root extract and *Scenedesmus rubescens* extract, and a moisturizing component comprising at least one alpha-hydroxy acid.

18. The skincare formulation prepared according to claim 17, wherein the antimicrobial component comprises silver citrate and zeolite blend.

19. The skincare formulation prepared according to claim 18, wherein the zeolite blend is at 5% relative to total net weight of the composition.

20. The skincare formulation prepared according to claim 17, wherein the antiaging component comprises at least one hydrolyzed sodium hyaluronate.

21. The skincare formulation prepared according to claim 17, and further adding an antioxidant component.

22. The skincare formulation prepared according to claim 17, and further adding a vitamin component.

23. The skincare formulation prepared according to claim 17, and further adding at least one copper ferment.

24. The skincare formulation prepared according to claim 17, wherein the alpha-hydroxy acid comprises at least one of lactic acid, tartaric acid, citric acid, malic acid, glycolic acid, gluconic acid, and salicylic acid.

25. The skincare formulation prepared according to claim 17, wherein the screen-emitted artificial visible light protecting component further comprises at least one of *Calendula officinalis* extract and niacinamide.

26. The skincare formulation prepared according to claim 17, wherein the antimicrobial component comprises at least one or more of: hypochlorous acid, oregano, benzalkonium chloride, aloe vera, peppermint extract, rosemary extract, ginger, Manuka honey, tea tree oil, *Coleus forskohlii* root oil, *Kaempferia galanga* root extract, *Olea europaea* leaf extract, *Curcuma longa*, zeolite, *Melia azadirachta*, *Camellia sinensis* leaf extract, silver, and colloidal silver.

27. The skincare formulation prepared according to claim 17, wherein the antiaging component comprises at least one or more of: *Dracaena cambodiana* leaf extract, *Saccharomyces* copper ferment, acetyl hexapeptide-3, acetyl hexapeptide-8, acetyl hexapeptide-20, palmitoyl pentapeptide, palmitoyl oligopeptide, tripeptide-1, acetyl tetrapeptide-9, vitamin C, vitamin A, vitamin E, reservatrol, coenzyme $Q_{10}$, niacinamide, polyphenols, flavonoids, glutathione, peony extract, malachite extract, hydrolyzed sodium hyaluronate, and hydrolyzed hyaluronate.

28. The skincare formulation prepared according to claim 17, wherein the moisturizing component comprises at least one or more of: lactic acid, tartaric acid, citric acid, malic acid, glycolic acid, gluconic acid, and salicylic acid.

29. A skincare formulation prepared by combining:

at least one alpha hydroxy acid selected from the group consisting of lactic acid, citric acid, tartaric acid, malic acid, glycolic acid, gluconic acid, salicylic acid and mixtures thereof;

at least one blue light mitigator selected from the group consisting of *Withania somnifera* root extract, *Calendula officinalis* extract, *Scenedesmus rubescens* extract, and niacinamide;

at least one hyaluronic acid selected from the group consisting of hydrolyzed sodium hyaluronate, hydrolyzed hyaluronic acid, sodium acetylated hyaluronate, and sodium hyaluronate;

at least one antioxidant selected from a group comprising at least *Saccharomyces* copper ferment; and at least one composition comprising silver citrate and zeolite blend.

30. The skincare formulation prepared according to claim 29, and further adding one or more ingredients selected from a group consisting of: a mixture of lactitol and xylitol with glycerin, *Calendula officinalis* extract, allantoin, niacinamide, panthenol, hyaluronic acid, prebiotics, probiotics, *Marrubium vulgare* extract, sodium PCA, sodium hyaluronate, hydrolyzed hyaluronate, a mixture of glycerin and pentylene glycol and *Rosmarinus officinalis* (rosemary) leaf extract and palmitoyl tetrapeptide-7 with chrysin, and combinations thereof.

31. A skincare formulation prepared by combining:

an antimicrobial component including silver citrate and zeolite blend;

an antiaging component comprising *Saccharomyces* copper ferment;

a moisturizing component comprising hydrolyzed sodium hyaluronate; and a screen-emitted artificial visible light protection component comprising at least one of *Withania somnifera* root extract and *Scenedesmus rubescens* extract.

32. The skincare formulation prepared according to claim 31, and further adding lactic acid.

33. The skincare formulation prepared according to claim 31, and further adding a sunscreen component.

34. The skincare formulation prepared according to claim 33, wherein the sunscreen component comprises one or more mineral ingredients.

35. The skincare formulation prepared according to claim 33, wherein the sunscreen component comprises zinc oxide.

* * * * *

UNITED STATES PATENT AND TRADEMARK OFFICE
CERTIFICATE OF CORRECTION

| | | |
|---|---|---|
| PATENT NO. | : 12,208,150 B2 | Page 1 of 1 |
| APPLICATION NO. | : 17/478773 | |
| DATED | : January 28, 2025 | |
| INVENTOR(S) | : Sonia Summers et al. | |

It is certified that error appears in the above-identified patent and that said Letters Patent is hereby corrected as shown below:

On the Title Page

At Item (73) Assignee: "Shielded, Beauty, LLC" should read --Shielded. Beauty, LLC--

Signed and Sealed this
Twenty-second Day of April, 2025

Coke Morgan Stewart
*Acting Director of the United States Patent and Trademark Office*